United States Patent [19]

DeMarco

[11] 4,309,991
[45] Jan. 12, 1982

[54] WRIST BRACE

[76] Inventor: Alexander H. DeMarco, 85 Maple Ave., Shelton, Conn. 06484

[21] Appl. No.: 160,910

[22] Filed: Jun. 18, 1980

[51] Int. Cl.³ ............................................. A61F 13/00
[52] U.S. Cl. .................................. 128/165; 273/54 B
[58] Field of Search ............. 128/165, 166; 273/54 B; 2/161 A

[56] References Cited

U.S. PATENT DOCUMENTS

| | | | |
|---|---|---|---|
| 3,238,939 | 3/1966 | Stubbs | 128/165 |
| 3,501,773 | 3/1970 | Stansberry et al. | 273/54 B |
| 3,512,776 | 5/1970 | Thomas, Sr. | 128/165 |
| 3,598,408 | 8/1971 | Klose | 128/165 |
| 3,815,908 | 6/1974 | Hashimoto | 128/165 |
| 3,871,029 | 3/1975 | Hollman | 273/54 B |

*Primary Examiner*—John D. Yasko
*Attorney, Agent, or Firm*—Walter Spruegel

[57] ABSTRACT

A wrist brace having a wrist holder and an attached fastener strap, of which the holder is in the form of a flat sleeve for slip-on application to a wrist, with the sleeve having a thumb aperture and a length which is split to form a wrist-covering cuff.

1 Claim, 6 Drawing Figures

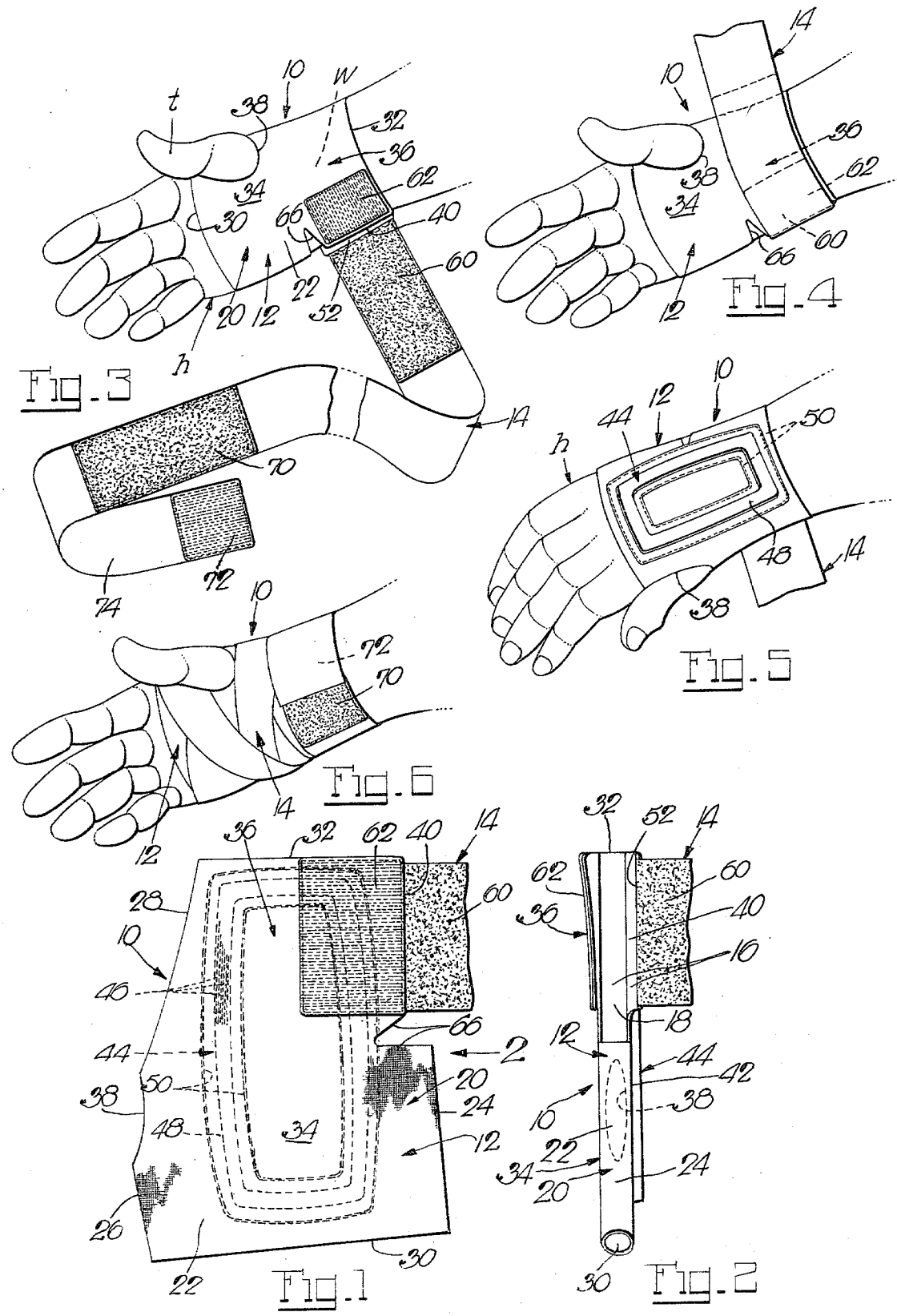

WRIST BRACE

This invention relates to wrist braces in general, and to ready-fit wrist braces in particular.

Human wrists are by nature among the most freely and widely flexible body joints, and they are also among the most frequently worked body joints in the course of many activities which they undergo alone or in concert with the immediately adjoining hands. While most operational working of wrists leaves them without adverse effects, there are also more unusual wrist actions such as stem from some strenuous sport and also other activities, for example, which may sprain or be otherwise potentially injurious to wrists unless they are effectively braced.

In order largely to mitigate, and preferably avoid altogether, adverse effects on wrists from overworking or otherwise abusing them, there have become known a number of wrist braces which have as their major parts a wrist holder in the form of a flat pad with a local stiffener, and attached fastener straps of one kind or another, of which the pad is applied by wrapping around a wrist, and the straps are wound around the applied pad. While these prior braces are satisfactory in most respects, they are also deficient in a few, though important, respects. Thus, displacement, more or less, of an applied pad on a wrist is likely to defeat effective bracing of the wrist and even cause discomfort to the same when in action. In this connection, such detrimental displacement of a pad on a wrist is likely to occur in the course of its application to the wrist, especially when a pad is so applied by the wearer himself or herself with only one free hand for well-placed and firm application of a brace to one's own wrist with only one free hand is quite a task in any event, and becomes a particularly awkward and difficult task when the hand so used is by nature the less dexterous one. Further, these prior braces largely rely on thumb apertures in the pads as chief anchors in locating the latter, with these apertures being arranged so that on slipping a pad with its aperture over the thumb on a hand, the pad will for its final location require mere turning on the protruding thumb to bring its stiffener into superposition on the back of the wrist. Once the pad is thus in its final position, the same is simply wrapped around the wrist and then held in place by winding the straps around the applied pad. However, it happens every so often, and especially when self-applying such a brace to one's own wrist, that in applying the pad in this fashion, the stiffener thereon will become displaced, more or less, on the wrist, and this is mostly due to fairly wide variations in the sizes of thumbs and according misfit of the latter in the tailored thumb apertures provided in the pads.

It is a primary object of the present invention to provide wrist braces which not only have none of the aforementioned deficiencies of the prior braces, but are also superior to the latter in most other respects.

It is another important object of the present invention to provide wrist braces with wrist holders and attached fastener straps, of which the wrist holders are formed largely as sleeves which are applied to wrists in typical slip-on fashion. In applying such a sleeve to a wrist, the same is slipped over the extended hand and onto the wrist in a manner quite as simple and smooth as slipping a glove onto a hand in a steady pull and without any twist, with the hand and sleeve being at the same time coordinated by bringing the stiffener into alignment with the back of the wrist for superposition thereon as required when the sleeve is in place on the wrist. Further, the sleeve of each wrist brace is normally held flat like a bottomless pocket and the stiffener is secured to one side thereof, so that on mere alignment of the outstretched fingers of a hand with such flat pocket and following straight pull of the sleeve over the hand and onto the wrist, the sleeve will accurately and quickly be located in bracing relation with the wrist. In fact, the flat pocket formation on the sleeve, in fittedly passing over the outstretched fingers of the wearer's hand, functions on a mere straight pull on the sleeve to lead the latter straight and without any twist over the hand and into correct position on the wrist. Finally, the sleeve is also provided with an aperture through which is extended the wearer's thumb in applying the sleeve to the wearer's wrist. Since the aforementioned flat pocket formation on the sleeve is mostly instrumental in leading the latter into correct, including non-twisted, position on a wrist on a mere pull on the sleeve, the thumb aperture in the sleeve does not appreciably contribute toward leading the latter onto a wrist. Instead, the thumb aperture, by exposing the thumb on the application of the sleeve to a wrist, permits manipulation and other use of the thumb alone or together with some or all of the fingers.

It is a further object of the present invention to provide wrist braces of which the aforementioned sleeves are split partway down along one side edge to form open cuff ends that facilitate the application of the sleeves to wrists by slip-on and also permit smooth finish application of the cuff ends to wrists.

Further objects and advantages will appear to those skilled in the art from the following, considered in conjunction with the accompanying drawings.

In the accompanying drawings, in which certain modes of carrying out the present invention are shown for illustrative purposes:

FIG. 1 is a side view of a wrist brace embodying the invention;

FIG. 2 is an end view of the same wrist brace as seen in the direction of the arrow 2 in FIG. 1; and FIGS. 3 to 6 show progressive steps, respectively, in applying to a hand a wrist brace according to the invention.

Referring to the drawings, and more particularly to FIGS. 1 and 2 thereof, the reference numeral 10 designates a wrist brace which has as its major components a sleeve-like body 12 and a fastener strap 14. The body 12 is in this instance formed of an inner ply 16 of a preferably knitted fabric 18 and an outer ply 20 of a preferably woven fabric 22, with these plies being laminated in any suitable manner, as by applying a coating of latex to their confronting faces and then pressing them together, for example. The fabric plies 16 and 20 are also stretchable and somewhat resilient, wherefore the body 12 has the same properties of stretchability and resiliency. The body 12 also lies normally flat (FIG. 2) owing in this instance to the press of the inner and outer plies 16 and 20 in the course of their lamination and ensuing formation of the sides 24, 26 and 28 which tend to keep the body flat.

The sleeve-like body 12, which is open at both ends 30 and 32, is tailored to form a sheath 34 and a cuff 36, of which the sheath 34 is closed on all sides and extends the length of the side edge 24 of the body, and the cuff 36 extends over the remaining length of the body and is open at the side 40 thereof, with the sheath 34 being also provided with a thumb aperture 38.

The body 12 is in this instance provided with a stiffener 44 (FIGS. 1 and 5) that may provide a plurality of bunched plastic stays 46 in an exemplary rectangular harness 48 which at 50 is suitably secured to the backside 42 of the body. The stiffener 44 has only limited yieldability in the direction of its length so as to be particularly effective in resisting abrupt backward overbending of the wrist which so frequently causes severe spraining and even breaking of the latter from such overbending in a fall or from any other accidental cause. The strap 14 of the brace 10 is suitably secured, as by sewing, for example, to the cuff part 36 of the sleeve-like body 12, and more particularly to the edge 52 at the open side 40 of the cuff part 36.

To apply the brace to the wrist w of a person's hand h, the sleeve-like body 12 is with its sheath part 34 lined up with the hand h and more particularly with the fingers thereof which are then preferably outstretched and held side by side for their ready passage into the sheath 34 in fair form-fit therewith on simply slipping the latter similarly as a glove over the fingers and succeeding palm part of the hand. In so slipping the body 12 onto the hand in a smooth straight pull, the thumb t on the hand, being already aligned with the aperture 38 by virtue of the prior initial orientation of the hand and body, will unfailingly lead into and emerge from the thumb aperture 38 and fully extend therefrom by the time the body 12 has been slipped onto the hand to the full extent shown in FIG. 3, i.e., when the cuff part 36 has been fully slipped over the wearer's wrist w and covers the same. The stiffener 44 is then also in proper bracing position on the backside of the hand (FIG. 5). Thus, the sleeve-like body 12 is, on its simple orientation with, and following precise glove-like slip onto, the wearer's hand, already applied to the hand to the near-finished extent shown in FIG. 3 in which only the strap remains to be applied, and such quick and effortless application of the body 12 to the hand is achieved regardless of whether the wearer himself or herself or an attendent applies the body.

Having applied the body 12 to the hand h in the described precise and expeditious manner (FIGS. 3 and 5), the application of the brace to the hand is concluded further expeditiously by wrapping the strap around the applied body 12. At the very start of thus wrapping the strap 14 around the applied body 12, a piece 60 of exemplary Velcro pile fabric at the innermost end of the strap is turned over and into engagement with a companion piece 62 of Velcro hook fabric at the cuff part 36 of the body 12, whereby these Velcro pieces interlock and thereby tack the cuff part of the body in a condition of close embrace of the wrist when the strap has been turned through only a small fraction of a turn. The body 12 is provided between its sheath and cuff parts 34 and 36 with a relief recess 66 to avoid bunching of the cuff part 36 on the wrist when tightening the former against the latter in applying the strap 14. FIG. 4 is similar to FIG. 3, except that in FIG. 4 the companion Velcro parts 60,62 are shown engaged and, hence, in interlock with each other. Having thus closed the cuff part 36 of the body 12 on the wrist by interlock of the Velcro parts 60 and 62, the strap 14 is wound around the applied body 12 in any manner desired by the wearer of the brace or by an attendant (FIG. 6). Finally, the outer end of the strap has spaced companion Velcro pieces 70 and 72 which are interlocked to hold the wrapped strap firmly against the body 12 by tightening the last turn 74 of the strap between the Velcro pieces 70 and 72.

What is claimed is:

1. A wrist brace, providing a normally flat tubular body of flexible material having opposite side edges and being open at both ends and forming over successive first and second lengths thereof a sheath and a cuff, respectively, with said sheath being circumferentially closed except for a thumb aperture intermediate said first length and along one of said edges, and said sheath being of a width for fitted reception of a length of the palm of a human hand and with the thumb in register with said aperture on widthwise slipping the body with the cuff leading over the fingers and palm and onto the wrist of the hand, and said other side edge of said body along said cuff being slit open and spaced inwardly from said other side edge along said sheath, a stiffener externally secured to the backside of the sheath and cuff, and strap means on said cuff for winding around said body.

* * * * *